(12) United States Patent
Ducharme

(10) Patent No.: US 8,454,584 B2
(45) Date of Patent: Jun. 4, 2013

(54) MEDICAL ANCHOR DEVICE

(75) Inventor: Richard W. Ducharme, Winston-Salem, NC (US)

(73) Assignee: Cook Medical Technologies LLC IN (US)

( * ) Notice: Subject to any disclaimer, the term of this patent is extended or adjusted under 35 U.S.C. 154(b) by 339 days.

(21) Appl. No.: 12/759,295

(22) Filed: Apr. 13, 2010

(65) Prior Publication Data

US 2011/0251642 A1    Oct. 13, 2011

(51) Int. Cl.
*A61B 17/00*    (2006.01)

(52) U.S. Cl.
USPC ............................................. 606/1; 600/562

(58) Field of Classification Search
USPC ............... 606/139, 159, 160, 232, 108, 1, 39, 606/72; 600/562, 564, 570
See application file for complete search history.

(56) References Cited

U.S. PATENT DOCUMENTS

| | | | |
|---|---|---|---|
| 68,647 A | 9/1867 | Palmer | |
| 2,072,346 A | 3/1937 | Smith | |
| 2,655,154 A * | 10/1953 | Richter | ......................... 606/159 |
| 4,517,965 A | 5/1985 | Ellison | |
| 4,738,255 A | 4/1988 | Goble et al. | |
| 4,774,948 A | 10/1988 | Markham | |
| 5,074,871 A | 12/1991 | Groshong | |
| 5,282,813 A | 2/1994 | Redha | |
| 5,449,355 A | 9/1995 | Rhum et al. | |
| 5,814,016 A | 9/1998 | Valley et al. | ..................... 604/96 |
| 6,514,248 B1 | 2/2003 | Eggers et al. | |
| 6,770,070 B1 * | 8/2004 | Balbierz | ........................ 606/41 |
| 7,056,294 B2 | 6/2006 | Khairkhahan et al. | |
| 2007/0010715 A1 | 1/2007 | Sixto, Jr. et al. | ............. 600/217 |
| 2007/0239162 A1 | 10/2007 | Bhatnagar et al. | ............. 606/69 |
| 2008/0177288 A1 | 7/2008 | Carlson | |

FOREIGN PATENT DOCUMENTS

FR        748666        7/1933

OTHER PUBLICATIONS

International Search Report and Written Opinion, PCT/US2011/031337, Jul. 19, 2011.

* cited by examiner

*Primary Examiner* — Victor Nguyen
(74) *Attorney, Agent, or Firm* — Brinks Hofer Gilson & Lione

(57) ABSTRACT

An endoscopically-deployable tissue-manipulation device including an elongate, generally tubular outer body having a proximal portion and a distal end portion that may be configured as sufficiently flexible to traverse the working channel of a flexible endoscope (e.g., side-viewing duodenoscope). The outer body may include an outer body lumen extending longitudinally between the proximal and distal portions. An anchoring structure of the device will include an elongate inner body that may extend through the outer body lumen and be configured to include a first linkage member attached to the inner body, a second linkage member that is pivotably attached to the first linkage member and to the outer body.

16 Claims, 8 Drawing Sheets

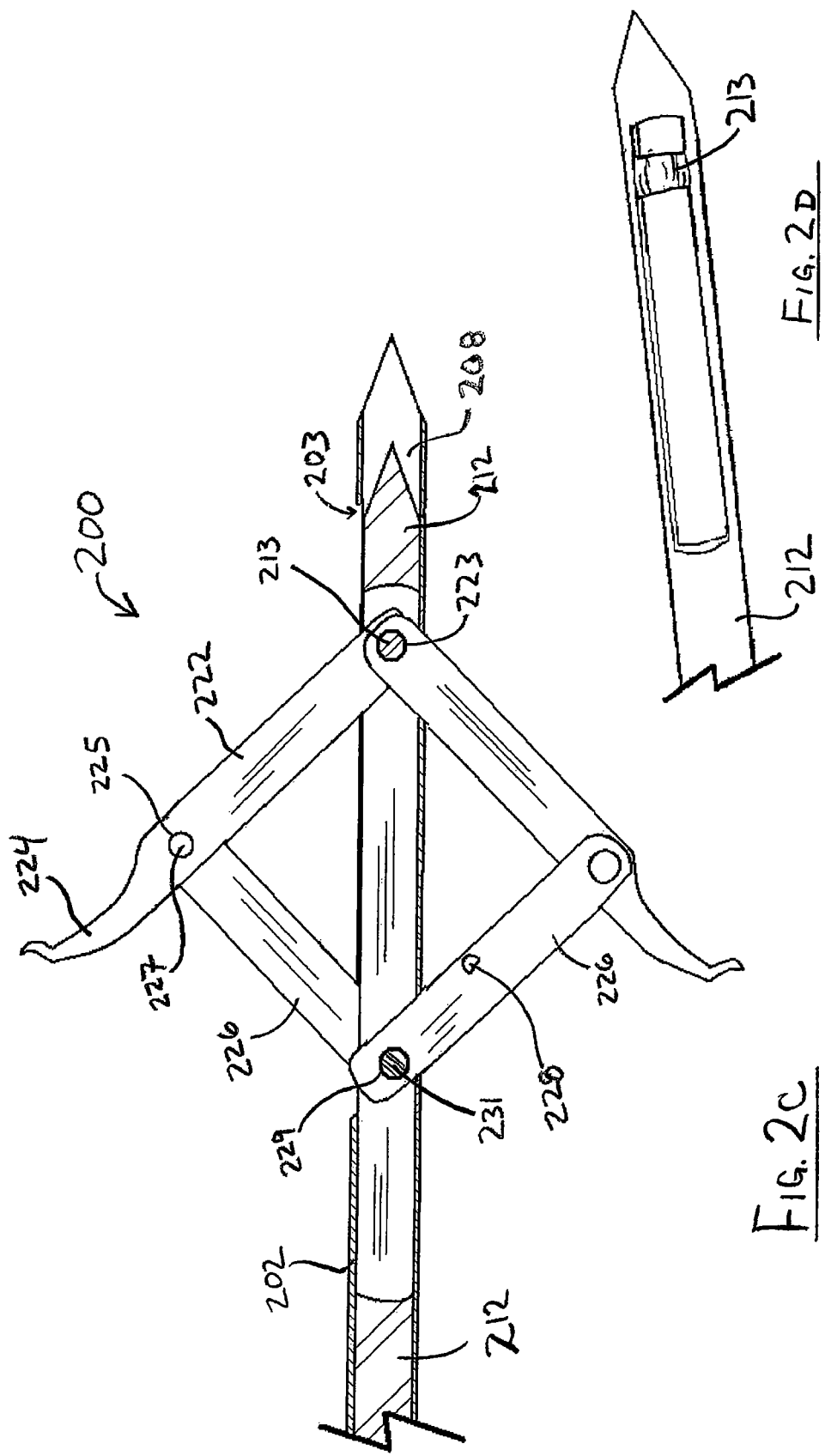

_US 8,454,584 B2_

MEDICAL ANCHOR DEVICE

TECHNICAL FIELD

The invention relates generally to medical devices. More particularly, the invention pertains to a catheter or cannula device equipped with a distal anchor mechanism.

BACKGROUND

In endoscopic procedures including, for example, endoscopic retrograde pancreatography (ERCP) procedures and natural orifice transluminal endoscopic surgery procedures, there is often a need for a physician to stabilize and/or retract tissue. This is often true in techniques where ultrasound visualization is being used and/or when other tools are to be introduced to and used in/on a target site. Various retractor devices have been used in open surgical procedures that are not readily adaptable to minimally invasive (e.g., endoscopic) surgical procedures.

There is a need to provide tools useful for retracting and/or stabilizing tissue during endoscopic surgical procedures, and particularly tools that may be deployed through the working channel of an endoscope (herein used generically to encompass endoscopes such as gastroscopes, duodenoscopes, laparoscopes, and other surgical visualization or ancillary devices used during minimally invasive surgical procedures).

BRIEF SUMMARY

Embodiments of the device disclosed herein preferably provide a low-profile device configured for introduction through a working channel of an endoscope, that is—configured with sufficient length, flexibility, pushability and trackability to be effectively used through a working channel of an endoscope such as, for example a gastric endoscope or duodenoscope. Embodiments of the device may be distally activated/deployed in a manner including an expanded profile (i.e., greater outermost circumferential profile) configured for stabilizing and/or retracting tissue. Certain embodiments may include echogenicity-enhancing features in or on their construction, configured to allow them to be more readily visualized under ultrasound. Preferred embodiments may be both expanded and retracted to facilitate use.

In one aspect embodiments of the present device may include an elongate, generally tubular outer body having a proximal portion and a distal end portion that may be configured as sufficiently flexible to traverse the working channel of a flexible endoscope (e.g., side-viewing duodenoscope). The outer body may include an outer body lumen extending longitudinally between the proximal and distal portions. An anchoring structure of the device will include an elongate inner body that may extend through the outer body lumen and be configured to include a first linkage member attached to the inner body, a second linkage member that is pivotably attached to the first linkage member and to the outer body. In preferred embodiments, at least one of the first or second linkage members includes an anchoring extension that extends from and beyond the pivotable attachment between the first and second linkage members. The anchoring structure may occupy a non-deployed first positional state wherein it is substantially within an outermost diameter of the outer body and a deployed second positional state wherein the inner body occupies a different longitudinal position relative to the outer body than in the first positional state, and wherein at least a portion of the first and second linkage members extends beyond the outermost diameter of the outer body. The outer body may be configured as a needle with a tissue-penetrating distal tip. The device may be used in a method wherein the device is introduced near a target area and advanced distal of tissue to be stabilized, or otherwise retracted, with the anchoring structure in the first positional state. After the device is thus oriented, the anchoring structure may be deployed to the second positional state and placed into contact with the tissue.

BRIEF DESCRIPTION OF THE DRAWINGS

FIGS. 2B and 2C show the device embodiment of FIG. 2A in a deployed configuration from external and longitudinal section views, respectively;

FIG. 2D shows a distal portion of the inner body of the device embodiment of FIG. 2A;

DETAILED DESCRIPTION

Figure 1A:
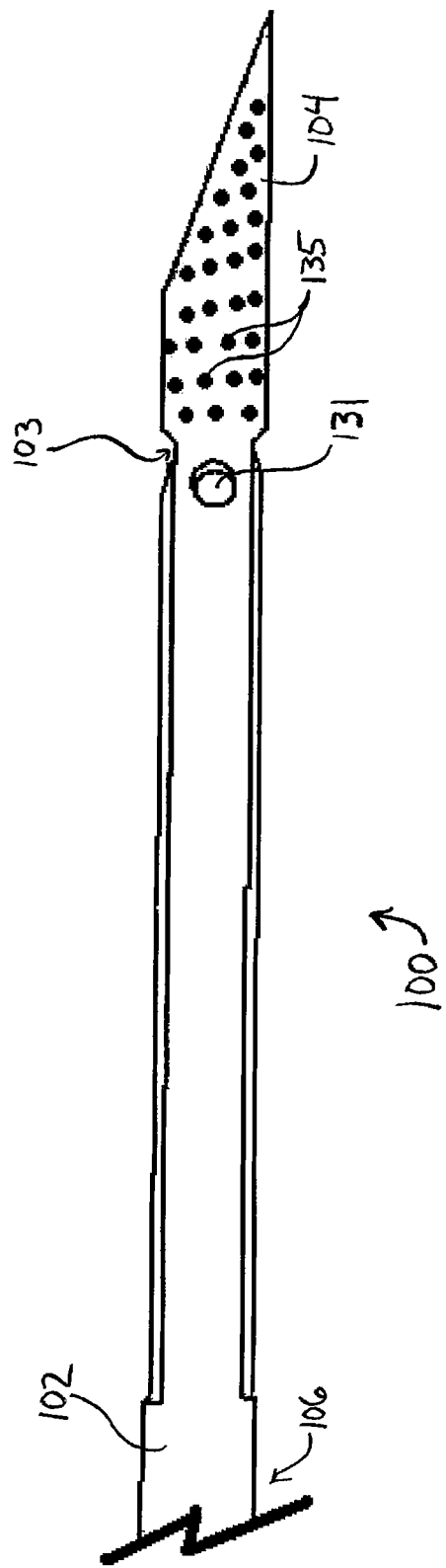
FIG. 1A shows a distal portion of an undeployed anchoring device embodiment from an external view.

The invention is described with reference to the drawings in which like elements are generally referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly. As used in the specification, the terms "proximal" and "distal" should be understood as being in the terms of a physician or other person operating a medical device or on a patient. Hence, the term "distal means the direction or portion of the device that is farthest from the physician or other person and the term "proximal" means the portion of the device that is nearest to the physician or other person.

Referring to FIGS. 1A-1D, an anchor device 100 is shown, including an elongate, generally tubular outer body 102 having a beveled distal tip 104 configured for penetrating tissue. The proximal portion 106 of the device 100 preferably extends back to a device handle (not shown, but which may be embodied as a needle handle now known or later developed in the art including, for example, a standard or modified three-ring handle, or a plunger style handle such as used with the Cook EchoTip® endoscopic ultrasound needles). The outer body 102 includes an outer body lumen 108 extending through at least a portion of its length. An elongate inner body 112 extends through the outer body lumen 108, and its proximal portion is at least partially longitudinally slidable relative to the outer body 102. The outer body 102 is attached to the inner body 112 by a pair of anchoring linkages 122, 126, which may be deployed through a side aperture 103 in the outer body 102.

Figure 1B:
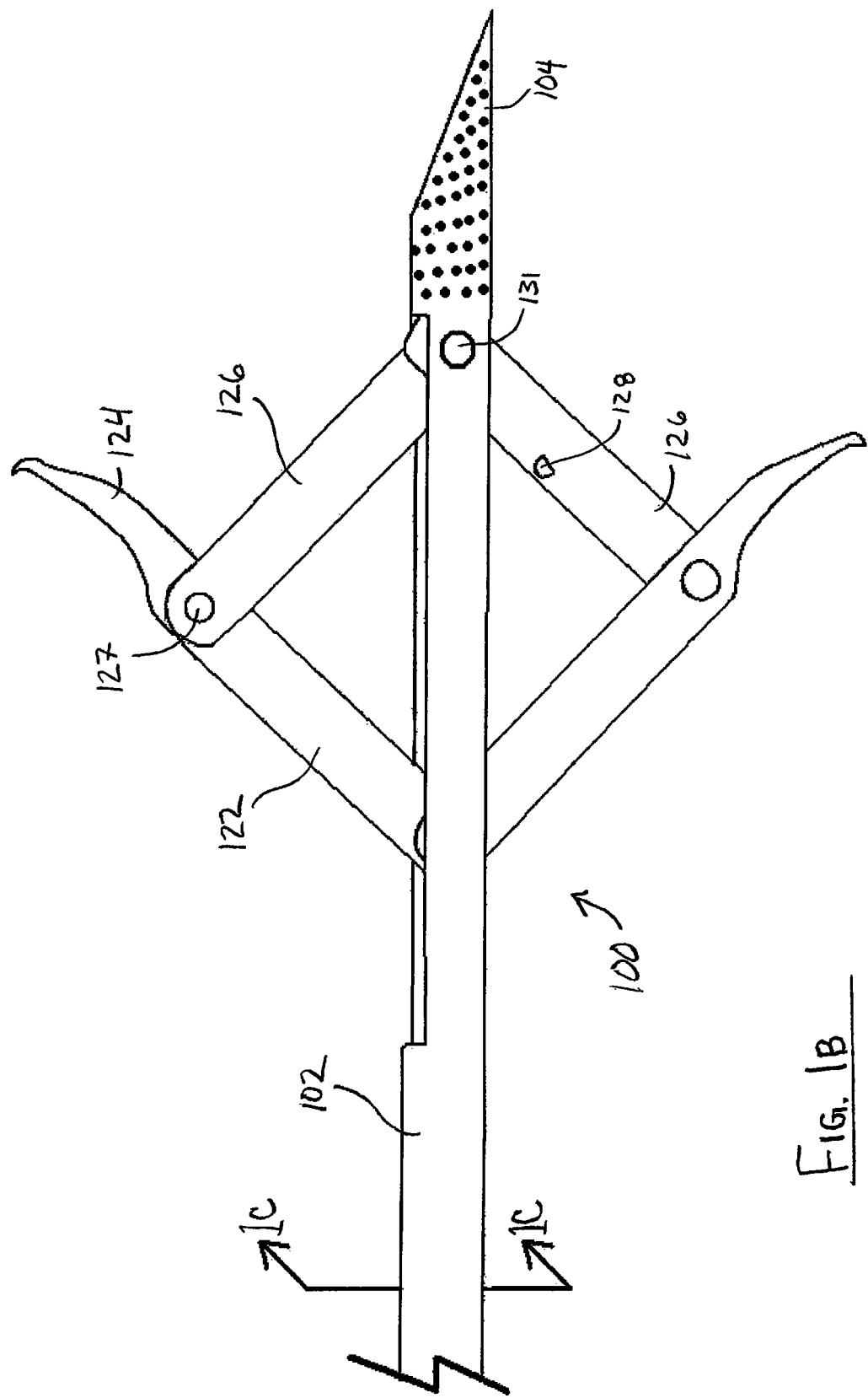
FIGS. 1B and 1C show the device embodiment of FIG. 1A in a deployed configuration from external and longitudinal section views, respectively.
Figure 1C:
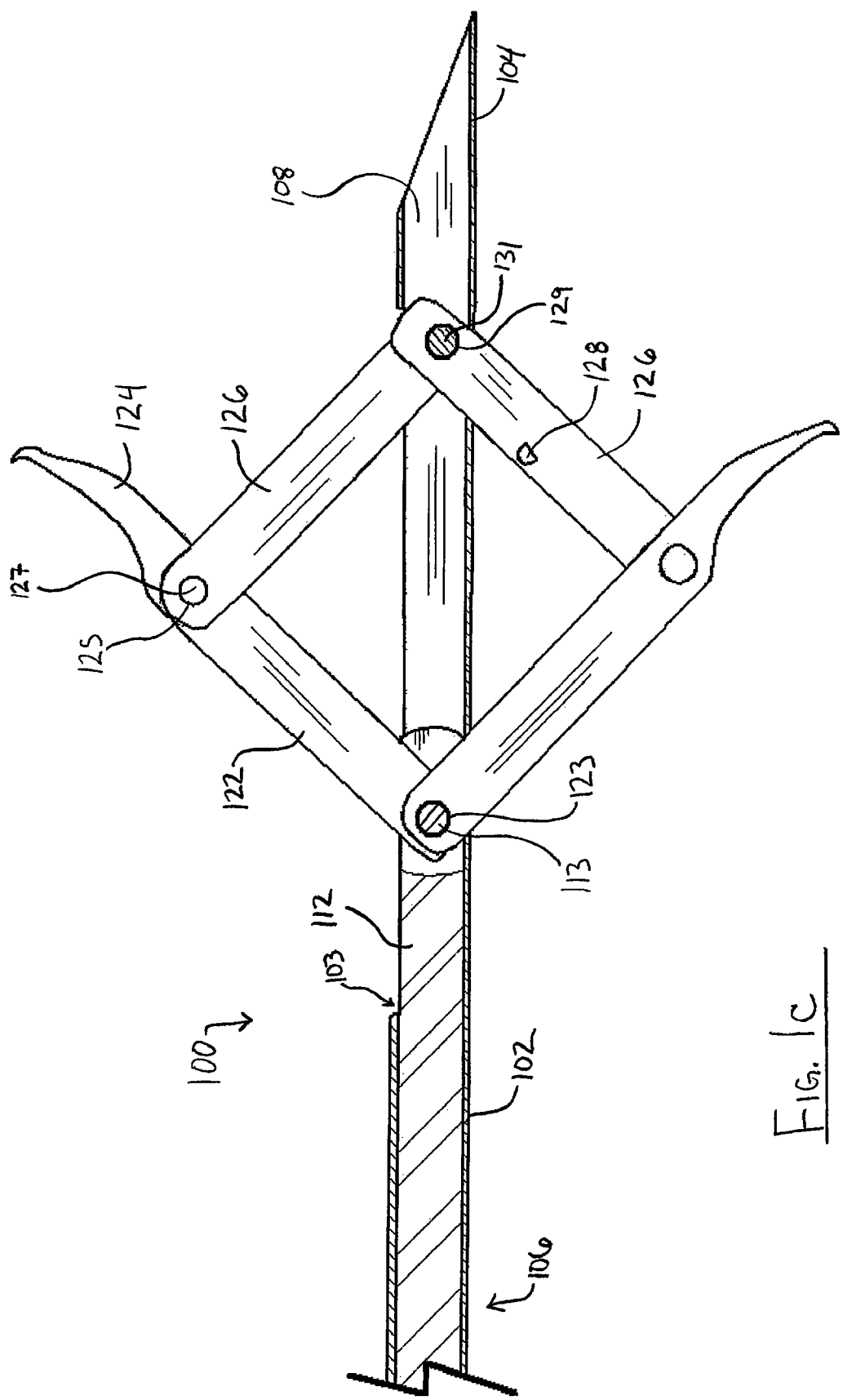
Figure 1D:
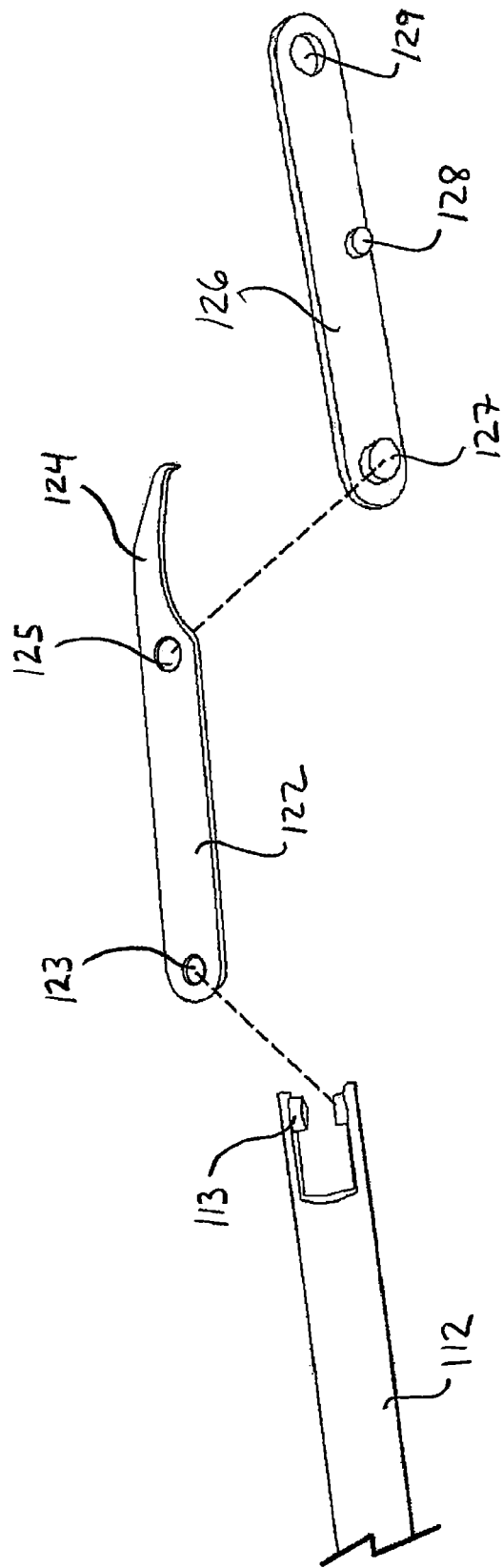
FIG. 1D shows linkage components of an anchoring structure of the device embodiment of FIGS. 1A-1C.

In the embodiment shown in FIGS. 1A-1D, the proximal linkage member 122 is pivotably attached to the inner body 112, which may be formed as a flexible or a rigid stylet. This connection is illustrated in FIG. 1C, which shows a longitudinal section view of the outer body 102 and inner body 112 (taken along line 1C-1C of FIG. 1B). A distal portion of the inner body 112 and the proximal and distal linkages 122, 126 are shown in FIG. 1D. The pivotable connection between the inner body 112 and the proximal linkage member 122 is depicted with the inner body including a forked distal end with a protruding boss 113 about which a proximal pivot aperture 123 of the proximal linkage member is pivotably fitted. The boss 113 may be flanged to help retain engagement with the proximal linkage member 123. Those of skill in the art will appreciate that the pivotable connections shown here with a pivot boss/pivot pin and corresponding aperture may be embodied in other manners known or developed in the art, all within the scope of the present invention.

The proximal linkage member 122 includes a distal pivot aperture 125. This distal pivot aperture 125 mates pivotably with a proximal linkage boss 127 on the distal linkage member 126. The distal end of the distal linkage member 126 includes a pivot opening 129 configured to receive and be pivotably mounted to an outer body pivot boss or pivot pin 131 (as shown in FIGS. 1A-1C). The proximal linkage member 122 includes an anchoring extension 124 configured to contact, retain, anchor, or otherwise manipulate tissue when it is deployed (the term "anchor" being used generically herein to capture all such actions). The distal end of the extension may include a hooked structure as shown to promote anchoring contact with tissue. This extension 124 extends beyond the pivoting attachment between the linkage members 122, 126. The distal linkage member 126 includes a retaining boss 128 configured to help align the linkage members and prevent their deployment in an undesired direction. The illustrations of FIGS. 1A-1C show a dual-anchor embodiment, but it will be appreciated that a single-anchor embodiment or other multi-anchor embodiments may be practiced within the scope of the present invention.

A method for deploying the anchor may be understood with reference to FIGS. 1A-1C. FIG. 1A shows a first positional state wherein the anchoring device 100 is not deployed. The inner body 112 is in a more proximal position, and the linkage members 122, 126 are generally aligned with the inner body 112 and each other substantially within an outermost diameter defined by the outer body 102. One deploys the anchor device 100 of this embodiment by moving the inner body 112 longitudinally distally to a second positional state relative to the outer body 102, which actuates the linkage members 122, 126. As shown in FIGS. 1B and 1C, distal advancement of the inner body 112 relative to the outer body 102 (or vice versa), rotates the proximal linkage 122 out of its centrally-aligned position such that its distal end including the anchoring extension 124 pivot relative to the inner body boss 113 and the distal linkage member 126, which also pivots out from the outer body 102. If desired, the device 100 may be configured and actuated to allow the anchoring extension 124 to pivot to being perpendicular or even pivoted/rotated past perpendicular relative to the longitudinal axis of the inner and outer bodies 112, 102.

The inner and outer bodies 112, 102 may be configured as rigid or flexible. As such, they may be configured for passage through the working channel of a medical imaging device, whether rigid (e.g., laparoscopy apparatus or the like) or flexible (e.g., end-viewing or side-viewing gastric endoscope or the like). In certain preferred embodiments, the device 100 will be dimensioned and sufficiently flexible to be used by passage through the working channel of an end-viewing or side-viewing gastro-intestinal endoscope. Anchoring device embodiments may also include echogenicity-enhancing features. As used herein, including in the claims, the terms "echogenic" and "echogenicity-enhancing" are defined as having or providing for enhanced echogenicity. Specifically, it is used to refer to materials or portions of materials that are constructed or are treated to provide greater reflectivity of ultrasonic waves than standard materials used for a sheath, cannula, catheter, and/or inner body (e.g., stylet or inner catheter), and to provide an echogenic profile relative to surrounding tissues during use in a patient body to accurately orient and direct the echogenic device portion. It is known in the art that most materials used for a sheath, catheter, cannula, or stylet will reflect some ultrasonic waves, but the term "echogenic," as used herein includes surfaces treated by creating a textured or patterned surface including, for example, one or more of dimples, divots, knurling, ridges, or the like—each of which is known in the art to enhance echogenicity as compared to a smooth surface for a similarly-sized/shaped object, (and/or, when specifically referenced, using a material known to provide an enhanced echogenic profile) configured to provide clear ultrasound visualization at a resolution providing for accurate location and navigation of a device in a body (e.g., of a patient). Echogenic construction of may be enhanced by surface texture, but can also be provided by structural inclusions such as embedded bubbles, beads, or other inclusions in a polymer or metal that can provide for a different ultrasound reflectivity than material surrounding them. A discrete surface region adjacent the distal end of the outer body 102 is shown with dimples 135.

Referring to FIGS. 2A-2D, an anchor device 200 is shown, including an elongate, generally tubular outer body 202 having a distal tip 204 tapered in a manner configured for penetrating tissue. The outer body 202 includes an outer body lumen 208 extending through at least a portion of its length. An elongate inner body 212 extends through the outer body lumen 208, and its proximal portion is at least partially longitudinally slidable relative to the outer body 202. The outer body 202 is attached to the inner body 212 by a pair of anchoring linkages 222, 226, which may be deployed through a side aperture 203 in the outer body 202.

Figure 2A:
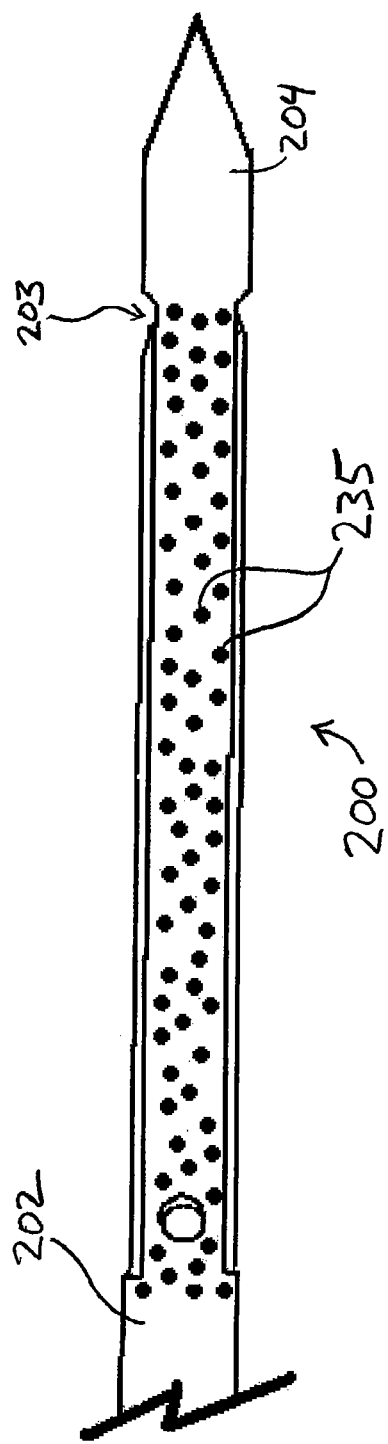
FIG. 2A shows a distal portion of another anchoring device embodiment, in an undeployed configuration, from an external view.

In the embodiment shown in FIGS. 2A-2D, the distal linkage member 222 is pivotably attached to the inner body 212, which may be formed as a flexible or a rigid stylet. This connection is illustrated in FIG. 2C, which shows a longitudinal section view of the outer body 202 and inner body 212 (taken along line 2C-2C of FIG. 2B). A distal portion of the inner body 212 is shown in FIG. 2D. The pivotable connection between the inner body 212 and the distal linkage member 222 includes an apertured distal end with an inner pivot pin/axle 213 about which a distal pivot aperture 223 of the distal linkage member is pivotably fitted. Those of skill in the art will appreciate that the pivotable connections shown here with a pivot boss/pivot pin and corresponding aperture may be embodied in other manners known or developed in the art, all within the scope of the present invention.

Figure 2B:
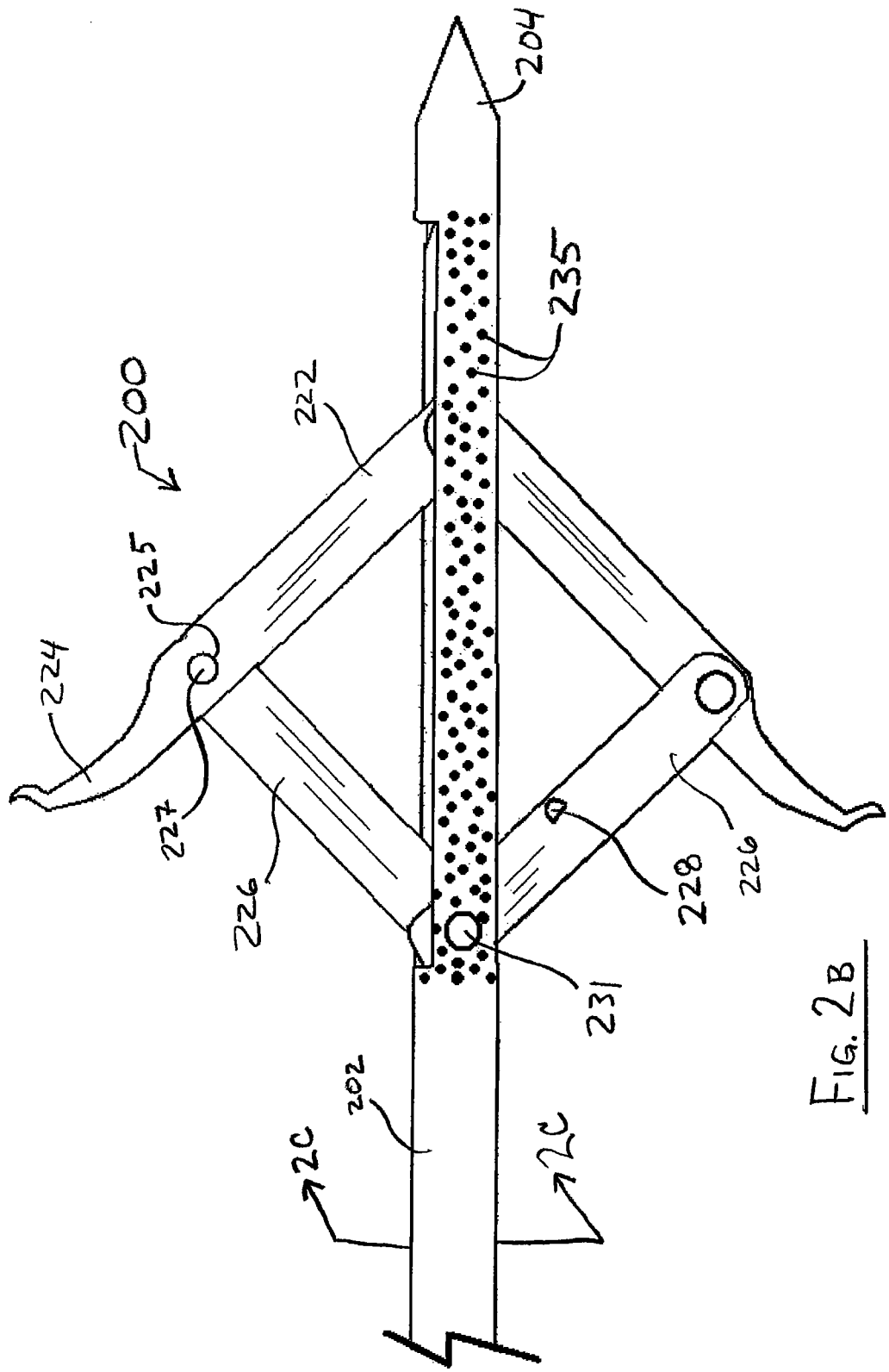

The distal linkage member 222 includes a proximal pivot aperture 225. This proximal pivot aperture 225 mates pivotably with a distal linkage boss 227 on the proximal linkage member 226. The proximal end of the proximal linkage member 226 includes a pivot opening 229 configured to receive and be pivotably mounted to an outer body pivot boss or pivot pin 231 (as shown in FIGS. 2A-1C). The distal linkage member 222 includes an anchoring extension 224 configured to contact, retain, anchor, or otherwise manipulate tissue when it is deployed. The proximal end of the extension may include a hooked structure as shown to promote anchoring contact with tissue. This extension 224 extends beyond the pivoting attachment between the linkage members 222, 226. One or both of the proximal linkage members 226 may include a retaining boss 228 configured to help align the linkage members and prevent their deployment in an undesired direction. The illustrations of FIGS. 2A-2C show a dual-anchor embodiment, but it will be appreciated that a single-anchor embodiment (see, e.g., FIGS. 3A-3B) or other multi-anchor embodiments may be practiced within the scope of the present invention.

A method for deploying the anchor may be understood with reference to FIGS. 2A-1C. FIG. 2A shows a first positional state wherein the anchoring device 200 is not deployed. The inner body 212 is in a more distal position, and the linkage members 222, 226 are generally aligned with the inner body 212 and each other substantially within an outermost diameter defined by the outer body 202. One deploys the anchor device 200 of this embodiment by moving the inner body 212 longitudinally proximally to a second positional state relative to the outer body 202, which actuates the linkage members 222, 226. As shown in FIGS. 2B and 2C, proximal movement of the inner body 212 relative to the outer body 202 (or vice versa), rotates the distal linkage 222 out of its centrally-aligned position such that its distal end including the anchoring extension 224 pivot relative to the inner body pivot axis 213 and the proximal linkage member 226, which also pivots out from the outer body 202. If desired, the device 200 may be configured and actuated to allow the anchoring extension 224 to pivot to being perpendicular or even pivoted/rotated past perpendicular relative to the longitudinal axis of the inner and outer bodies 212, 202.

The inner and outer bodies 212, 202 may be configured as rigid or flexible. As such, they may be configured for passage through the working channel of a medical imaging device, whether rigid (e.g., laparoscopy apparatus or the like) or flexible (e.g., end-viewing or side-viewing gastric endoscope or the like). In certain preferred embodiments, the device 200 will be dimensioned and sufficiently flexible to be used by passage through the working channel of an end-viewing or side-viewing gastro-intestinal endoscope. A discrete surface region adjacent the anchoring structure and the side opening 203 of the outer body 202 is shown with an echogenic pattern 235.

Figures 3A, 3B:
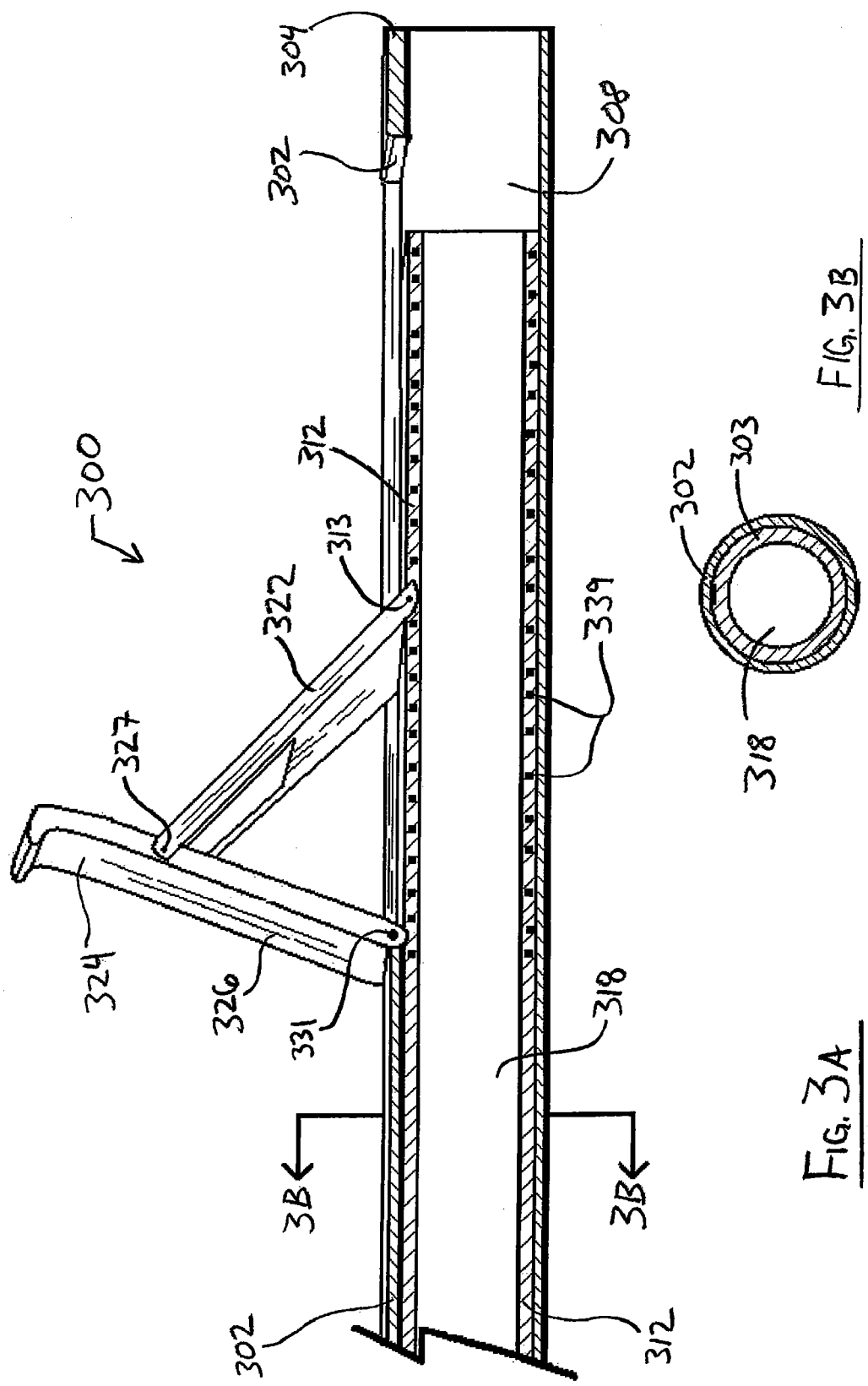
FIG. 3A shows a distal portion of yet another anchoring device embodiment from a longitudinal section view, including partial top perspective of the device's deployed configuration.
FIG. 3B shows a transverse section view of the device embodiment of FIG. 3A.

Referring to FIG. 3A-3B, an anchor device 300 is shown, including an elongate, generally tubular outer body 302 having a generally blunt distal tip 304. FIG. 3A shows a partial perspective view of the device in longitudinal section, and FIG. 3B shows a transverse section view along line 3B-3B of FIG. 3A. The outer body 302 includes an outer body lumen 308 extending through at least a portion of its length. An elongate inner body 312 extends through the outer body lumen 308, and its proximal portion is at least partially longitudinally slidable relative to the outer body 302. The inner body includes an inner body lumen 318. The outer body 302 is attached to the inner body 312 by a pair of anchoring linkages 322, 326, which may be deployed through a side aperture 303 in the outer body 302.

In the embodiment shown in FIGS. 3A-1D, the distal linkage member 322 is pivotably attached to the inner body 312, which may be formed as a flexible or a rigid stylet. The connection between the inner body 312 and the distal linkage member 322 is depicted with the distal linkage member 322 pivotably disposed about a distal pivot axis 313. Those of skill in the art will appreciate that the pivotable connections shown here with a pivot boss/pivot pin and corresponding aperture may be embodied in other manners known or developed in the art, all within the scope of the present invention.

The distal linkage member 322 mates pivotably about a central pivot axis 327 with the distal linkage member 326. The proximal end of the proximal linkage member 326 is pivotably mounted to the outer body 302 about a proximal pivot axis 331. The proximal linkage member 322 includes an anchoring extension 324 configured to contact, retain, anchor, or otherwise manipulate tissue when it is deployed. The distal end of the extension may include a hooked structure as shown to promote anchoring contact with tissue. This extension 324 extends beyond the pivoting attachment between the linkage members 322, 326. The illustrations of FIGS. 3A-3B show a single-anchor embodiment. A method for deploying the anchor structure may be effected in the same manner as described with reference to FIGS. 1A-1C.

The inner body lumen 318 preferably is configured to allow for passage of other surgical tools or devices therethrough (e.g., wire-guided devices, biopsy forceps, catheter devices, etc.). The wall of the inner body 312 is shown as including an echogenicity-enhancing feature in the form of echogenic inclusions 339 embedded therein.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:
1. An anchor device, comprising:
an elongate, generally tubular outer body including
 a proximal portion,
 a distal end, and
 an outer body lumen extending longitudinally between the proximal portion and distal end;
an elongate inner body extending through a length of the outer body lumen;
wherein the inner body includes at least one anchoring structure comprising
 a first linkage member pivotably attached to the inner body, and
 a second linkage member pivotably attached to the outer body and pivotably attached to the first linkage member;
wherein at least one of the first and second linkage members includes an anchoring extension configured to anchor body tissue, the anchoring extension configured to extend from its linkage member generally longitudinally beyond the pivotable attachment between the first and second linkage members; and
a first positional state wherein the anchoring structure is substantially within an outermost diameter of the outer body and a second positional state where the anchoring structure extends beyond the outermost diameter of the outer body, wherein the second positional state comprises the inner body occupying a different longitudinal position relative to the outer body than the first positional state; and wherein the inner and outer bodies are configured with sufficient flexibility for passage through a working channel of a side-viewing gastro-intestinal endoscope.

2. The anchor device of claim 1, wherein the outer body is configured as a needle, comprising a penetrating distal tip.

3. The anchor device of claim 1, wherein the first linkage member is located proximal of the second linkage member.

4. The anchor device of claim 1, wherein the inner and outer bodies are configured with sufficient flexibility for passage through a working channel of a medical imaging device.

5. The anchor device of claim 1, further comprising an inner body lumen longitudinally disposed through the inner body.

6. The anchor device of claim 1, wherein the inner lumen is configured for passage of a surgical device.

7. The anchor device of claim 1, wherein the outer body comprises a tapered distal end.

8. The anchor device of claim 1, wherein at least one of the linkage members comprises a retaining detent configured to prevent pivoting rotation in one direction.

9. The anchor device of claim 1, wherein at least one of the inner body and the outer body comprises an echogenicity-enhancing feature.

10. The anchor device of claim 9, wherein the echogenicity-enhancing feature is disposed in a discrete region adjacent the distal end.

11. The anchor device of claim 9, wherein the echogenicity-enhancing feature is disposed in a discrete region adjacent the anchoring structure.

12. The anchor device of claim 1, wherein the distal end is configured as a needle with a tissue-penetrating distal tip and further comprising an echogenicity-enhancing feature.

13. The anchor device of claim 12, wherein the echogenicity-enhancing feature is disposed in a discrete region adjacent the tissue-penetrating distal tip.

14. The anchor device of claim 12, wherein the echogenicity-enhancing feature is disposed in a discrete region adjacent the anchoring structure.

15. A method for manipulating tissue using the anchor device of claim 1, the method comprising the steps of:
    directing the distal end through a tissue desired to be manipulated sufficiently that the anchoring structure is distal of the tissue;
    actuating the inner body longitudinally relative to the outer body to occupy the second positional state wherein the anchoring structure extends beyond the outermost diameter of the outer body; and
    contacting the tissue with the anchoring structure.

16. The method of claim 15, further comprising retracting the tissue proximally.

* * * * *